(12) United States Patent
Brewer

(10) Patent No.: US 6,638,248 B1
(45) Date of Patent: Oct. 28, 2003

(54) RETRACTABLE SYRINGE

(76) Inventor: Roy Tudor Brewer, 109 Capper Street, Gayndah, Queensland, 4625 (AU)

( * ) Notice: Subject to any disclaimer, the term of this patent is extended or adjusted under 35 U.S.C. 154(b) by 19 days.

(21) Appl. No.: 09/830,571

(22) PCT Filed: Sep. 11, 2000

(86) PCT No.: PCT/AU00/01088

§ 371 (c)(1),
(2), (4) Date: Jun. 13, 2001

(87) PCT Pub. No.: WO01/17594

PCT Pub. Date: Mar. 15, 2001

(30) Foreign Application Priority Data

Sep. 9, 1999 (AU) ............................................. 47486/99

(51) Int. Cl.[7] .............................................. A61M 5/00
(52) U.S. Cl. ...................................... 604/110; 604/195
(58) Field of Search ................................ 604/181, 195, 604/196, 197, 198, 221, 222, 228, 229, 110, 192

(56) References Cited

U.S. PATENT DOCUMENTS

| | | | | |
|---|---|---|---|---|
| 4,507,117 A | * | 3/1985 | Vining et al. ................ | 604/196 |
| 4,675,005 A | * | 6/1987 | DeLuccia .................... | 604/110 |
| 5,000,736 A | | 3/1991 | Kaufhold, Jr. et al. | |
| 5,125,898 A | | 6/1992 | Kaufhold, Jr. et al. | |
| 5,180,370 A | * | 1/1993 | Gillespie ..................... | 604/110 |
| 5,205,824 A | * | 4/1993 | Mazur ......................... | 604/110 |
| 5,273,539 A | * | 12/1993 | Chen ........................... | 604/110 |

FOREIGN PATENT DOCUMENTS

| | | |
|---|---|---|
| WO | WO 91/10461 | 7/1991 |
| WO | WO 92/18186 | 10/1992 |

* cited by examiner

*Primary Examiner*—Manuel Mendez
(74) *Attorney, Agent, or Firm*—Hoffman, Wasson & Gitler, PC

(57) ABSTRACT

A hypodermic syringe having a barrel with an open end, a base end and an internal bore; a needle assembly including a needle base member located inside the bore and releasably engaged with the base end and a needle which protrudes through the base end of the barrel; a plunger slidable within the bore, the plunger having a piston releasably engaged therewith and a chamber having air evacuated therefrom, the chamber being sealed at one end by the piston; wherein the piston includes means for engaging the needle base member such that in use when the plunger is depressed and the piston approaches the base end of the barrel, the piston can engage the needle base member, the needle base member is released from the base end and the piston is released from the plunger such that the piston needle base member and needle can be forced into the chamber by atmospheric pressure, wherein the needle base member is releasably engaged with the base end of the barrel by means of a split ring movable from an engagement position to a release position.

10 Claims, 1 Drawing Sheet

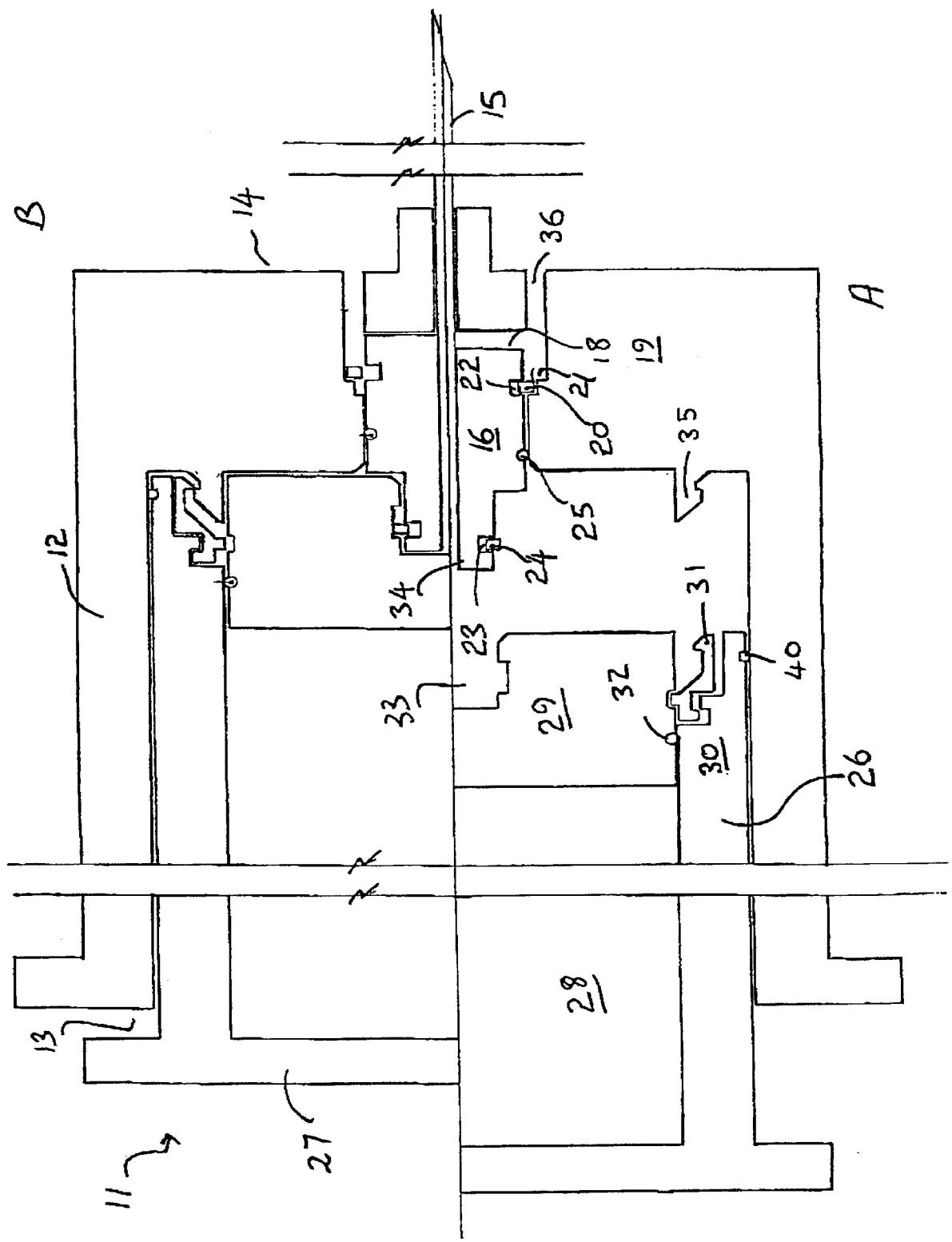

RETRACTABLE SYRINGE

FIELD OF THE INVENTION

The present invention is directed towards a syringe having a retractable needle.

BACKGROUND OF THE INVENTION

Syringes in which the needles are able to be retracted into the syringe barrel after use are known.

Such syringes have been developed in order to reduce the risk of needle-stick injuries experienced by health professionals. Typically these earlier syringes provide means by which the syringe piston can engage the needle base at the end of the injection procedure. The piston and needle can then be withdrawn into the barrel of the syringe by the user. A disadvantage of such syringes is that in the withdrawn position, the end of the plunger extends from the open barrel of the syringe. If the end of the plunger is accidentally depressed, the needle may be pushed out of the barrel. In order to avoid this occurring complicated locking arrangements for locking the plunger in the withdrawn position have been proposed. Typical locking arrangements have a twist-lock mechanism.

A further disadvantage of these syringes is that withdrawal of the plunger and needle into the syringe barrel and subsequent locking action is a two handed operation. Thus, the ultimate safety of the syringe is subject to the method of operation of the user. An error in operation may result in incomplete withdrawal of the needle into the barrel and/or failure to securely lock the needle within the barrel.

In order to overcome the disadvantages of the manually operable single use syringes, syringes which automatically withdraw the needle into the body of the plunger after fluid delivery have been developed.

Typically, the piston engages the base of the needle and is then withdrawn into the body of the piston. Withdrawal may be actuated by a spring or by air pressure in which case the body of the piston has an evacuated chamber.

For withdrawal of the needle and plunger to occur, the needle and plunger must be released from the syringe barrel and piston respectively. Further, the piston must be able to engage the base of the needle. There have been a number of different arrangements which have been proposed to provide the respective engagement and needle release means. Examples of such arrangements include rupturable membranes or frangible members which can fracture so as to release either the needle or the piston. Other arrangements include complex claw arrangements whereby claws are deformed at the end of the depression stroke of the plunger to either release and/or engage the respective parts.

A major disadvantage of these arrangements is that they are quite complicated and include a large number of parts. This makes the syringes complicated and expensive to manufacture. However, a particular disadvantage is that the mechanism must operate when the needle is inserted into the flesh of a patient In the above mechanisms, a reasonable amount of force is required to rupture or deform the various parts so as to activate the withdrawal mechanism. Such force may be greater than that normally required during a normal delivery stroke of the plunger. Any increase in downwards force on the plunger at the end of fluid delivery has potential to injure or inflict pain or discomfort to a patient. Also, the necessity to use additional force at the end of an injection may be undesirable during procedures such as spinal injections.

OBJECT OF THE INVENTION

It is therefore an object of the invention to provide a syringe which may at least partially overcome the above disadvantages or provide the public with a choice.

SUMMARY OF THE INVENTION

According to a broad form of the invention there is provided a hypodermic syringe having;

a barrel with an open end, a base end and an internal bore;

a needle assembly including a needle base member located inside the bore and releasably engaged with the base end and a needle which protrudes through the base end of the barrel;

a plunger slidable within the bore. the plunger having a piston releasably engaged therewith and a chamber having air evacuated therefrom, the chamber being sealed at one end by the piston; wherein the piston includes means for engaging the needle base member such that in use when the plunger is depressed and the piston approaches the base end of the barrel, the piston can engage the needle base member, the needle base member is released from the base end and the piston is released from the plunger such that the piston, needle base member and needle can be forced into the chamber by atmospheric pressure, wherein the needle base member is releasably engaged with the base end of the barrel by means of a split ring movable from an engagement position to a release position.

The needle base member is releasably engaged to the base of the barrel by a split ring moveable from an engagement to a release position. Typically, the split ring Is located between opposing recesses in the needle base member or the base of the barrel, thereby locking the two components together. Typically either the base member or recess has a second recess, deeper than the first recess spaced from the first recess in the direction of plunger travel. Typically, the second and first recesses are connected to form a stepped recess.

In use, the split ring can be moved such that It expands or contracts into the second recess (depending upon whether it is on the barrel or the needle base member) thereby releasing the needle base member from engagement with the barrel.

The syringe of the present invention includes a plunger releasably attached to a piston. The piston has an evacuated chamber which is sealed at one end by the piston. The piston is releasably engaged with the plunger. The plunger may be engaged by any suitable means which will allow the piston to be released from the plunger when the piston meets the needle base at the termination of the plunger stroke.

Preferably, the piston Is also releasably engaged to the plunger by a split ring. Preferably, the plunger further includes means for locking the plunger to the base end of the barrel when the plunger is fully depressed. This locking mechanism locks the plunger inside the barrel and prevents withdrawal of the plunger and also re-use of the syringe. The locking mechanism may include any suitable arrangement and may include one or more projections or recesses located on the plunger or barrel and one or more complimentary recesses or projections located on the other of the barrel or plunger. The locking mechanism preferably includes a split ring. The split ring may be the same split ring which releasably engages the plunger and piston. In this case, upon release of the piston, the split ring can engage an inwardly facing locking projection located on the base and of the barrel.

According to a further embodiment of the present invention, there is provided a hypodermic syringe having;

a barrel with an open end, a base end and an internal bore and a locking means at the base end;

a needle assembly including a needle base member located inside the bore and releasably engaged with the base end and a needle which protrudes through the base end of the barrel;

a plunger slidable within the bore, a piston releasably engaged with the plunger and a chamber having air evacuated therefrom, the chamber being sealed at one end by the piston; wherein the piston includes means for engaging the needle base member such that in use, when the plunger is depressed and the piston approaches the base end of the barrel, the piston engages the needle base member, the needle base member is released from the base end, the plunger releases the piston and is simultaneously engaged by the locking means at the base end of the barrel; such that the piston, needle base member and needle are forced into the chamber by atmospheric pressure and the plunger remains engaged with the barrel means so that it may not be removed from the bore.

In either embodiment, the piston is released from the plunger, the difference in air pressure forces the plunger back inside the evacuated chamber. Typically, there is a seal between the piston and chamber walls such that the piston can be retained inside the chamber by atmospheric pressure. Typically the barrel may include one or more air inlets at the base end. These air inlets facilitate withdrawal of the piston into the chamber.

BRIEF DESCRIPTION OF THE DRAWING

FIG. 1 illustrates a schematic cross sectional view of a preferred syringe 1 of the present invention.

DESCRIPTION OF THE PREFERRED EMBODIMENT

Section A of the FIGURE illustrates the syringe towards the completion of the fluid injection procedure. Section B Illustrates the syringe at the end of the injection procedure.

The syringe 11 includes a barrel 12 having a bore. The barrel is open at one end 13. The base 14 of the barrel is adapted to retain a needle 15. The needle 15 is firmly held by a needle base member 16. The needle base member 16 is housed within an aperture 18 in the wall 19 at the base 14 of the barrel. The needle base member 16 is held In place within aperture 18 by split ring 20. The split ring 20 is located between opposed recesses 21, 22 in the needle base member 16 and wall 19 of the barrel respectively. The recess 22 is a step expansion recess having a depth of half the cross sectional thickness of the split ring.

The needle base member includes a further recess 23, also fitted with a split ring 24. The purpose of this split ring will be described below.

When the syringe 11 is assembled, split rings 20, 24 are entered into recesses 21, 23 in the needle base member 16. The needle base member 16 and attached needle 15 are inserted into barrel 12 through opening 13 until split ring 20 is aligned with recess 21. An O ring 25 provides a fluid seal between the needle base member 16 and barrel wall 19.

The syringe 11 also includes a plunger 26. The plunger 26 has a head 27 which extends from the open end 13 of barrel 12. The plunger 26 is slidable within the bore of the barrel 12. The plunger 26 has an evacuated chamber 28. The chamber 28 is sealed at one end by a piston 29. The piston 29 is releasably attached to the plunger wall 30 by a multi-function split ring 31. An O ring 32 provides a gas and fluid seal between the plunger 26 and piston 29. A further O ring 40 provides a seal between the plunger 28 and barrel wall.

The syringe 11 is initially operated in a manner similar to conventional syringes. The barrel is charged with a injectable fluid and the fluid is injected by depressing plunger 26. Section A illustrates the relative position of the syringe components as the plunger 26 is almost fully depressed. Plunger 26 includes means for engaging the needle base member 16. The means for engaging the needle base member includes a recess 33, in piston 29, which is complimentary to and receives the end of the needle base member 16 and where a split ring 24 expands within recess 33. As the plunger is depressed further, the piston 29 meets the needle base member 16 and the base wall 19 of the barrel 12. The piston 29 has a recess 33 which is complementary to the shape of the end 34 of the needle base member 16. As the piston 29 is urged towards the needle base member, the recess 33 receives the end 34 of the needle base member and engages split ring 24. Split ring 24 expands within the recess and locks the piston 29 to the needle base member 16.

Further depression of the plunger 26 forces the needle base member 16 towards the base wall 19 of the barrel 12 as illustrated in section B. The base 36 of barrel 12 has an annular locking projection 35. As the piston 29 is depressed, split ring 31 comes into contact with locking projection 35. This causes the split ring 31 to fully expand which releases the piston 29 from plunger 26. Further depression of plunger 26 forces split ring 31 to engage locking projection 35 so as to effectively lock the plunger 26 and barrel wall together.

Downwards pressure of the plunger 26 on the needle base member 16 pushes the needle base member into the position shown in B. Split ring is pushed downwards along the stepped portion of recess 21 allowing it to expand, thereby disengaging from recess 22 in the needle base member 16 and releasing the needle base member from the barrel.

When the piston 29 is released from the plunger 26, the plunger 26 and engaged needle base member are forced into evacuated chamber 28 by air pressure. Air inlets 36 are provided in the barrel base to facilitate movement of the piston in response to the difference in air pressure. The difference in air pressure between the chamber 28 and the atmosphere assists in maintaining the piston 26, needle base member 16 and needle 15 within the chamber 28.

It can be seen that in the above embodiment the needle is rapidly and automatically withdrawn into the plunger body. Such withdrawal does not required two handed operation and does not rely on correct operation by the user. At the completion of the action, all components are locked together, and the needle is safely secured within the plunger body.

It can also be seen that the needle base member can be released from the barrel without requiring the rupturing or deformation of any members by force.

The split ring is under compression and it is released of part of the compression force which expands the split ring. The only force input required by the operation is that required to slide the ring along the step of the recess in the barrel wall. Typically, this force will be essentially the same as that required for movement of the plunger. In other words, the needle base member may be released as part of the normal downward stroke of the plunger. The other split rings operate sequentially in a similar manner to reduce the amount of force required to engage and release the various parts as compared to earlier syringes.

It will be appreciated that various changes and modifications may be made to the above embodiment without departing from the spirit and scope of the invention.

I claim:

1. A hypodermic syringe having;
    a barrel with an open end, a base end and an internal bore;
    a needle assembly including a needle base member located inside the bore and releasably engaged with the base end and a needle which protrudes through the base end of the barrel;
    a plunger slidable within the bore, the plunger having a piston releasably engaged therewith and a chamber having air evacuated therefrom, the chamber being sealed at one end by the piston; wherein the piston includes means for engaging the needle base member such that in use when the plunger is depressed and the piston approaches the base end of the barrel, the piston can engage the needle base member, the needle base member is released from the base end and the piston is released from the plunger such that the piston, needle base member and needle can be forced into the chamber by atmospheric pressure, wherein the needle base member is releasably engaged with the base end of the barrel by means of a split ring movable from an engagement position to a release position.

2. The syringe of claim 1, wherein the needle base member has a recess which receives the split ring when the split ring is in the engagement position.

3. The syringe of claim 2 wherein the needle base member is spaced from the base end of the barrel and when the plunger approaches and contacts the base end, the plunger pushes the needle base member towards the lock end of the barrel, so as to cause the split ring to move in the direction of plunger travel and allows it to expand out of the recess in the needle base member.

4. The syringe of claim 1, wherein the piston is releasably engaged with the plunger by means of a split ring.

5. The syringe of claim 4, wherein the plunger includes means for locking the plunger to the base end of the barrel when the plunger is depressed.

6. The syringe of claim 5, wherein the locking means includes a split ring which is initially located on the plunger, the base end of the barrel includes an inwardly facing locking projection and the spilt ring moves to engage the locking projection when the plunger is depressed.

7. The syringe of claim 6, wherein the split ring which locks the locking projection is the same split ring which releasably engages the piston and the plunger.

8. A hypodermic syringe having;
    a barrel with an open end, a base end and an internal bore and a locking means at the base end;
    a needle assembly including a needle base member located inside the bore and releasably engaged with the base end and a needle which protrudes through the base, end of the barrel;
    a plunger slidable within the bore, a piston releasably engaged with the plunger and a chamber having air evacuated therefrom the chamber being sealed at one end by the piston; wherein the piston includes means for engaging the needle base member such that in use when the plunger is depressed and the piston approaches the base end of the barrel, the piston engages the needle base member, the needle base member is released from the base end, the plunger releases the piston and simultaneously engaged by the locking means at the base end of the barrel; such that the piston, needle base member and needle are forced into the chamber by atmospheric pressure and the plunger remains engaged with the barrel so that it may not be removed from the bore.

9. The syringe of claim 8, which includes air inlets at the base end of the barrel.

10. A hypodermic syringe having:
    a barrel with an open end, a base end and an internal bore;
    a needle assembly including a needle base member releasably engaged with the base end and a needle which protrudes from the base end of the barrel;
    a plunger slidable within the bore, the plunger having a piston head releasabley engaged therewith and a chamber having air evacuated therefrom, the chamber being sealed at one end by the piston; wherein the piston includes means for engaging the needle base member such that in use when the plunger is depressed and the piston approaches the base end of the barrel, the piston engages the needle base member and, the needle base member is released from engagement with the base end of said barrel and the piston is thereafter released from, the engagement with the plunger whereby the piston, needle base member, and needle are forced into the chamber by atmospheric pressure.

* * * * *